United States Patent
Wandke et al.

(10) Patent No.: US 10,932,352 B2
(45) Date of Patent: Feb. 23, 2021

(54) FLAT PAD STRUCTURE

(71) Applicant: CINOGY GMBH, Duderstadt (DE)

(72) Inventors: Dirk Wandke, Heilbad Heiligenstadt (DE); Mirko Hahnl, Berlingerode (DE); Karl-Otto Storck, Duderstadt (DE); Melanie Ricke, Katlenburg-Lindau (DE); Leonhard Trutwig, Duderstadt (DE)

(73) Assignee: CINOGY GMBH, Duderstadt (DE)

( * ) Notice: Subject to any disclaimer, the term of this patent is extended or adjusted under 35 U.S.C. 154(b) by 0 days.

(21) Appl. No.: 16/617,586

(22) PCT Filed: Apr. 23, 2018

(86) PCT No.: PCT/DE2018/100388
§ 371 (c)(1),
(2) Date: Nov. 27, 2019

(87) PCT Pub. No.: WO2018/219383
PCT Pub. Date: Dec. 6, 2018

(65) Prior Publication Data
US 2020/0187341 A1    Jun. 11, 2020

(30) Foreign Application Priority Data

May 31, 2017  (DE) ..................... 10 2017 111 902.7

(51) Int. Cl.
*H05H 1/24* (2006.01)
*A61L 2/00* (2006.01)
(Continued)

(52) U.S. Cl.
CPC .......... *H05H 1/2406* (2013.01); *A61L 2/0011* (2013.01); *A61L 2/26* (2013.01);
(Continued)

(58) Field of Classification Search
CPC ... H05H 2001/2418; H05H 2001/2412; H05H 2001/2425; H05H 2001/2437
See application file for complete search history.

(56) References Cited

U.S. PATENT DOCUMENTS 6,413,255 B1   7/2002  Stern
2013/0345620 A1  12/2013  Zemel
(Continued)

FOREIGN PATENT DOCUMENTS

DE   10 2011 105 713 A1   12/2012
DE   10 2015 118 372 A1    9/2016
(Continued)

*Primary Examiner* — Alexander H Taningco
*Assistant Examiner* — Borna Alaeddini
(74) *Attorney, Agent, or Firm* — W&C IP

(57) ABSTRACT

A flat pad structure, designed to generate a dielectric barrier discharge plasma on a contact side (109) of said pad structure, comprises a flat electrode arrangement (112) which is embedded in a flat dielectric (102), can be supplied with high-voltage signals and is shielded on all sides against an unimpeded current flow; said pad structure has better stability and can be better adapted to elongate treatment areas because a width of the structure extends in a longitudinal direction (L) and in the longitudinal direction (L) the structure has a plurality of identically structured portions (101), each with a dielectric portion in the width of the pad structure and each with at least one electrode portion; the electrode portions of said portions (101) adjoin one another in the longitudinal direction (L) and form an electrode arrangement (112) extending over the entire length such that, in order to reduce the size of the contact surface in the longitudinal direction (L), at least one portion (101) can be separated from an adjacent portion (101) at a predetermined separation line (103) extending transverse to the longitudinal direction (L) and such that in the remaining portion (101) the predetermined separation line (103) is covered by an insulating component (116).

17 Claims, 7 Drawing Sheets

(51) Int. Cl.
*A61L 2/26* (2006.01)
*A61N 1/04* (2006.01)
*A61N 1/44* (2006.01)

(52) U.S. Cl.
CPC ............ *A61N 1/0492* (2013.01); *A61N 1/44* (2013.01); *A61L 2202/11* (2013.01); *A61L 2202/14* (2013.01); *H05H 2001/2418* (2013.01)

(56) References Cited

U.S. PATENT DOCUMENTS

| | | |
|---|---|---|
| 2014/0182879 A1 | 7/2014 | Busse |
| 2015/0157870 A1* | 6/2015 | Kalghatgi ......... H01J 37/32348 |
| | | 604/23 |
| 2016/0113701 A1 | 4/2016 | Zemel |
| 2016/0262251 A1* | 9/2016 | Jung ........................ H05H 1/24 |
| 2016/0331989 A1 | 11/2016 | Cho |
| 2017/0136252 A1* | 5/2017 | Weltmann ................ A61N 1/44 |
| 2017/0231680 A1* | 8/2017 | Mahrenholz ............. A61N 1/44 |
| | | 606/34 |
| 2019/0193863 A1* | 6/2019 | Abdollahzadehsangroudi ............ |
| | | B64C 23/005 |

FOREIGN PATENT DOCUMENTS

| | | |
|---|---|---|
| EP | 2 723 447 B1 | 4/2014 |
| EP | 3 051 926 A1 | 8/2016 |
| KR | 101 709 167 B1 | 2/2017 |
| WO | WO-2018162003 A1 * | 9/2018 ............... A61N 1/44 |

* cited by examiner

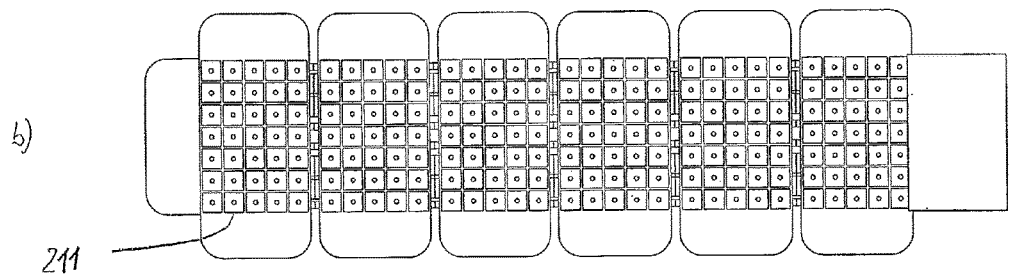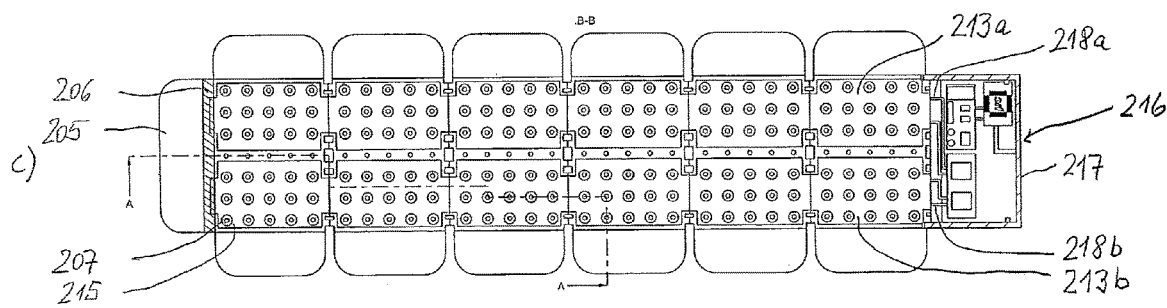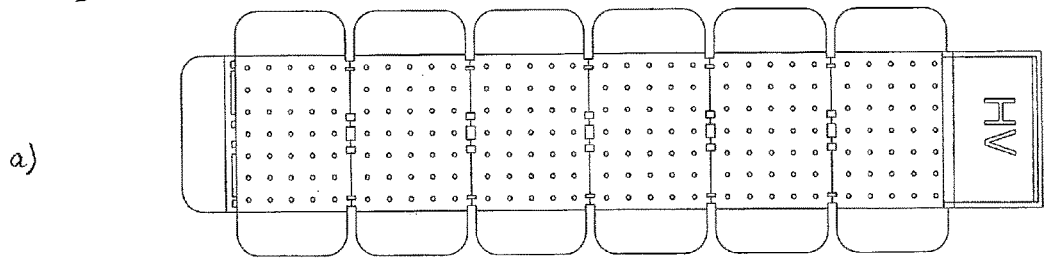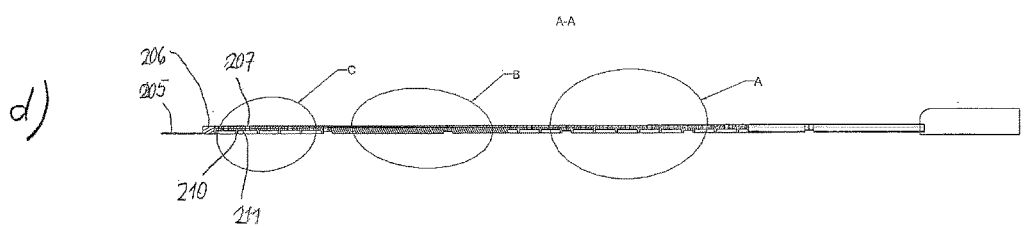
Fig. 2

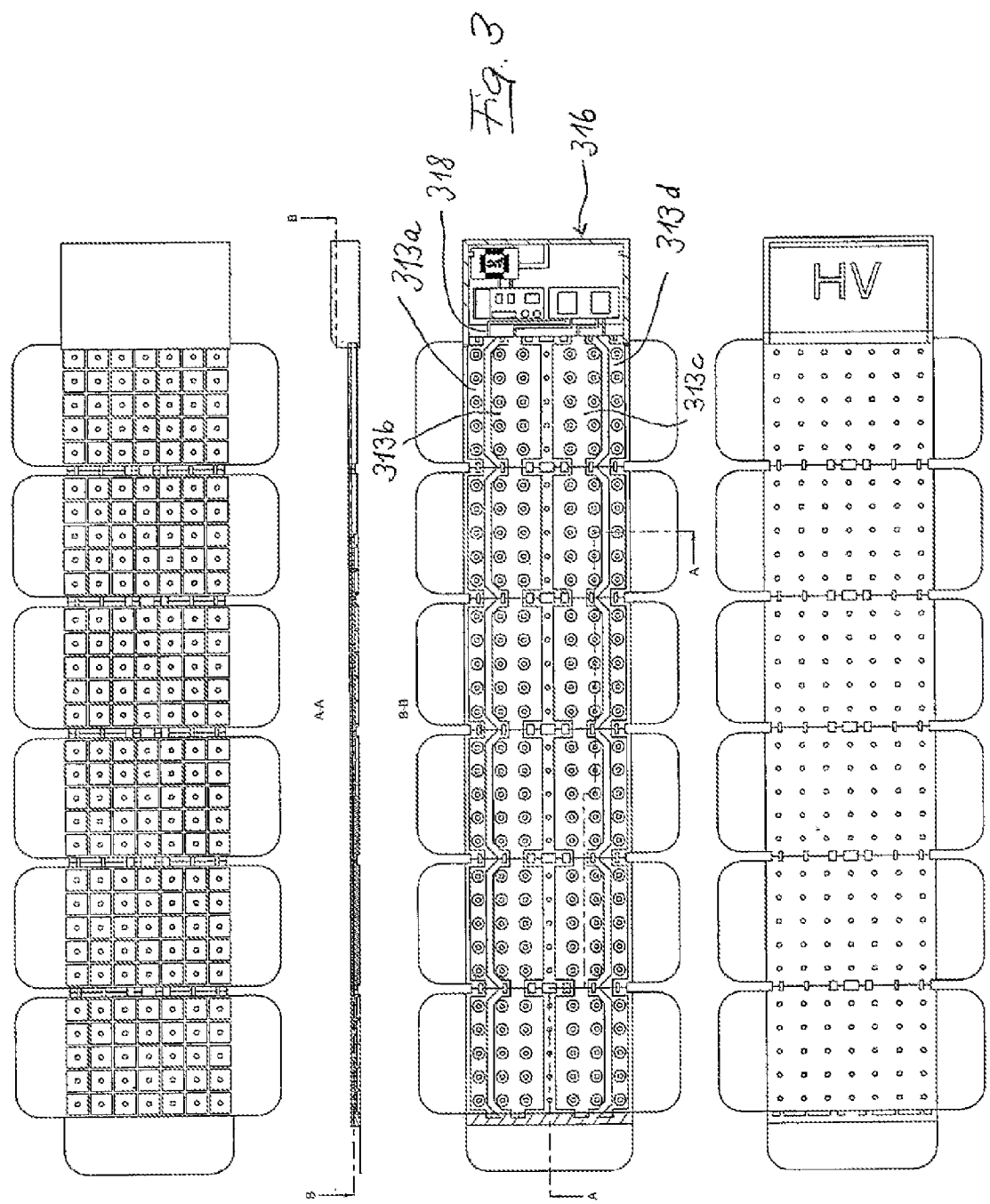

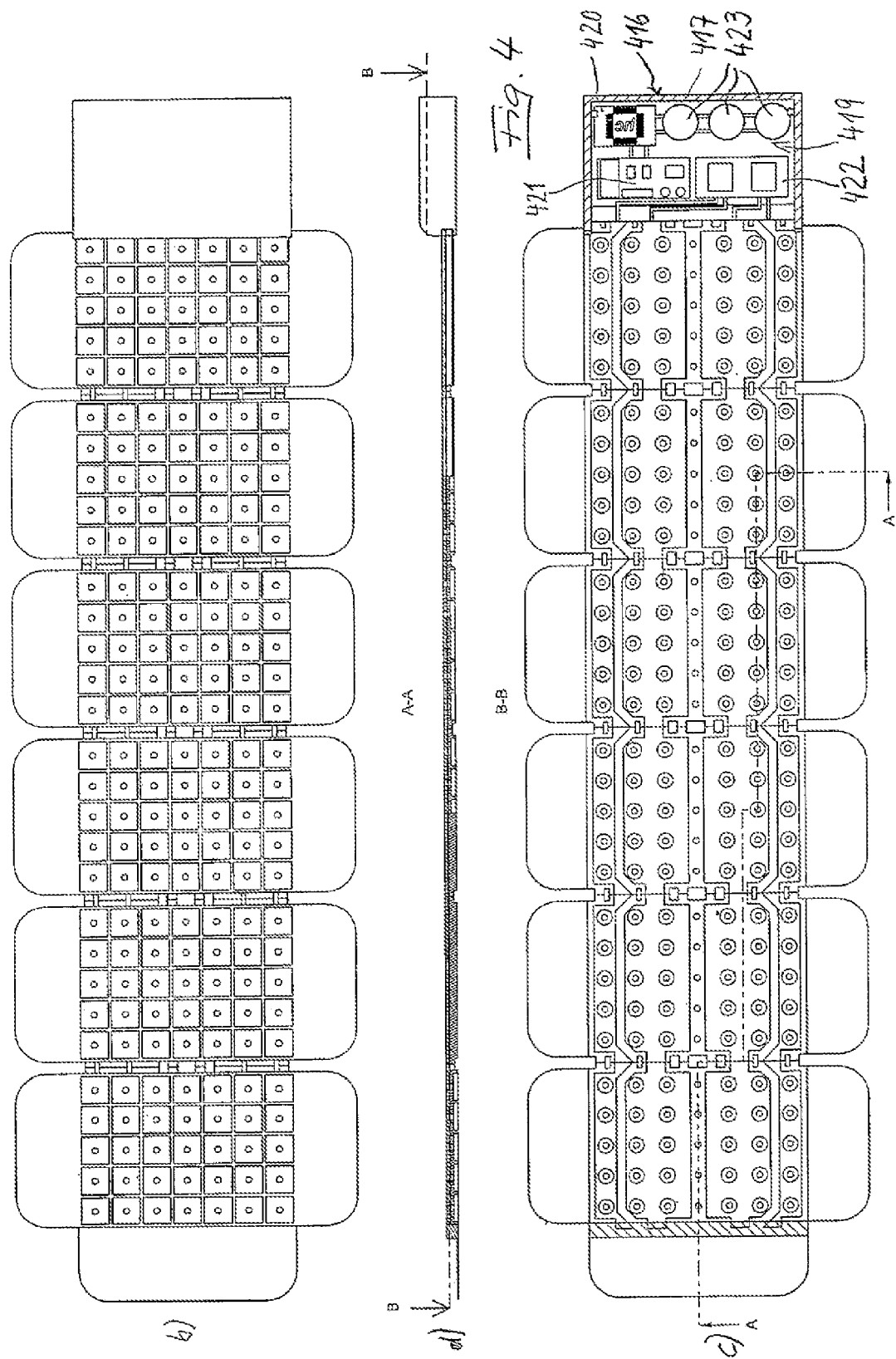

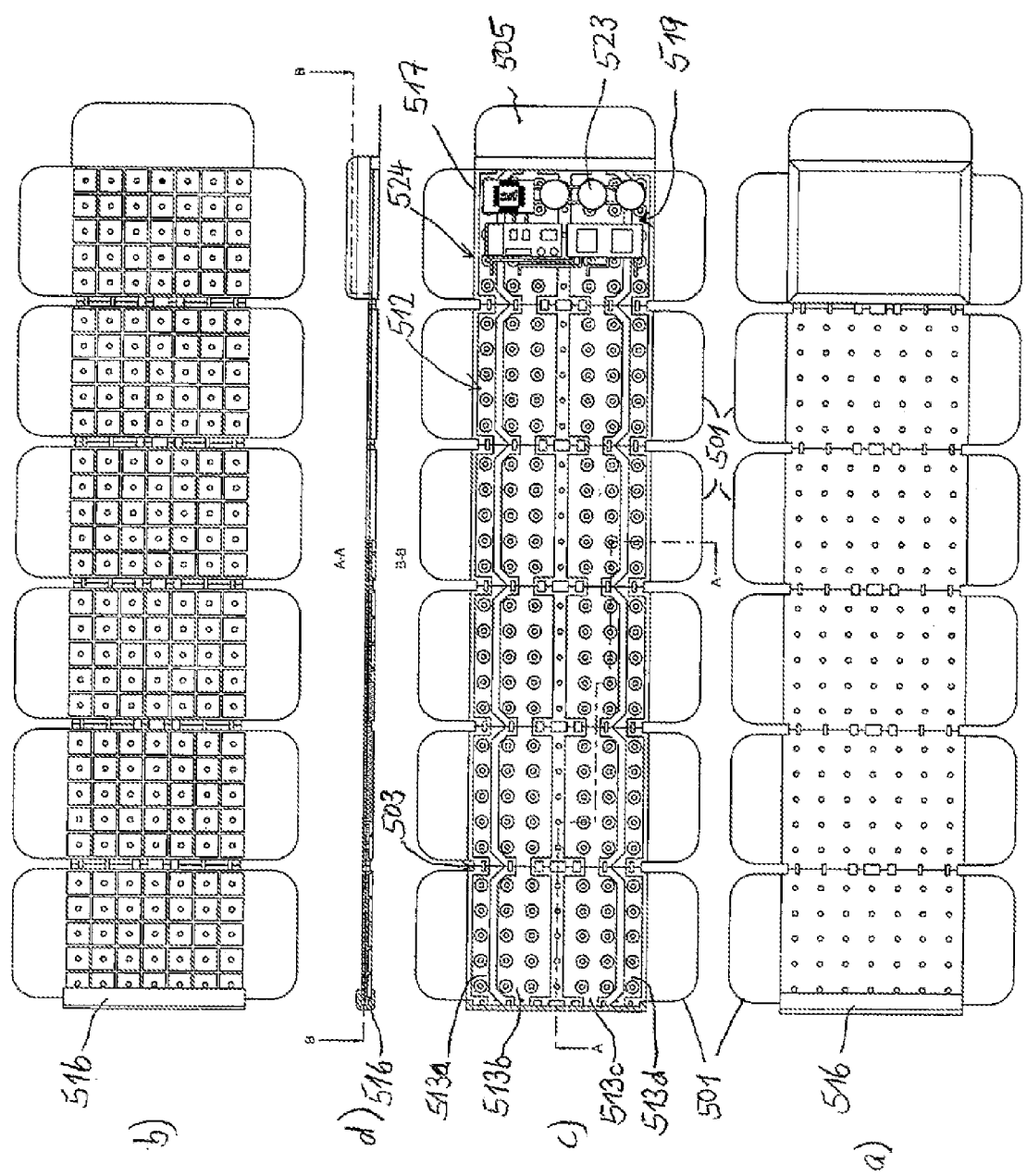

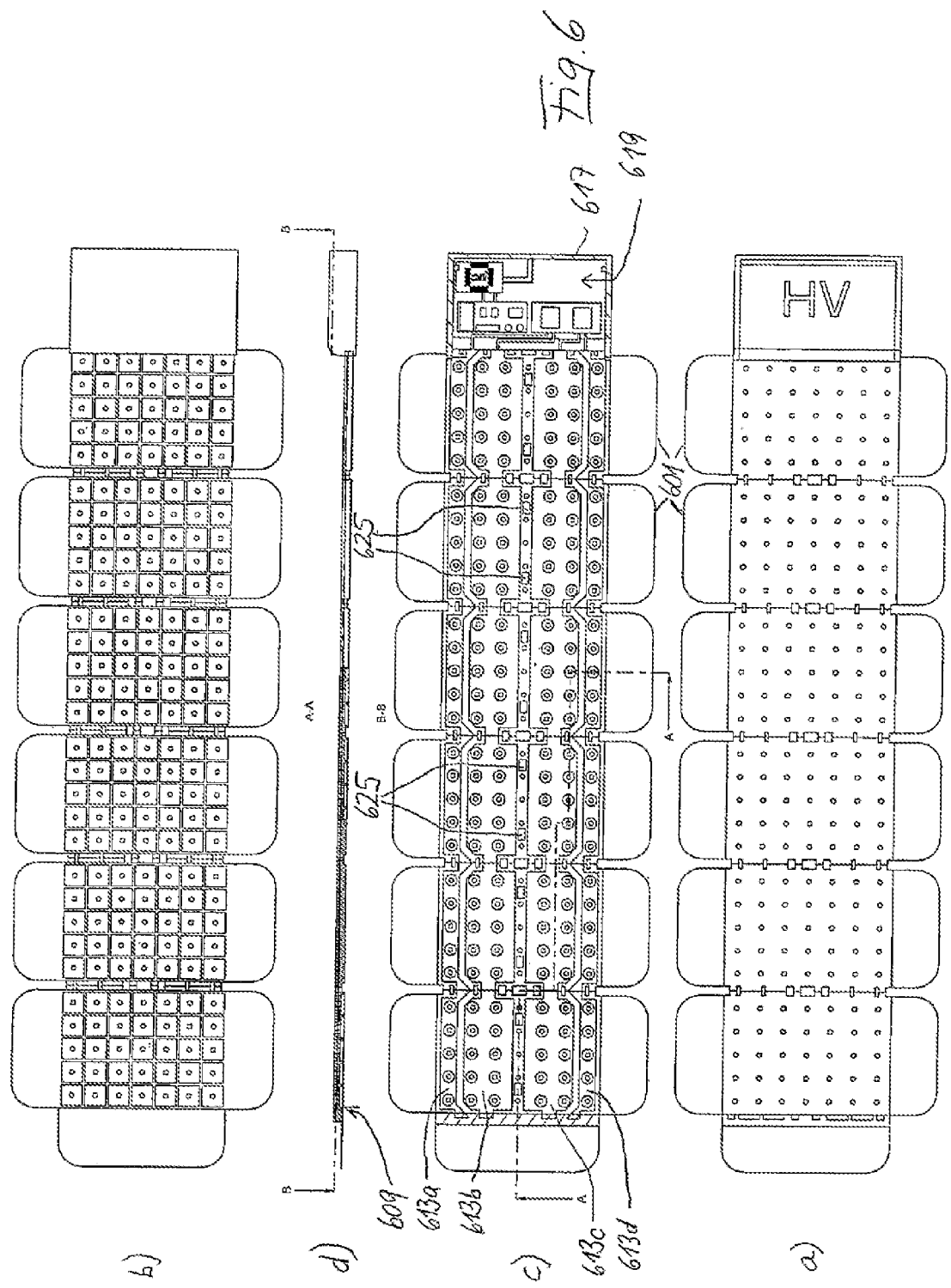

FLAT PAD STRUCTURE

The invention relates to a planar contact arrangement formed for generating a dielectric barrier plasma on an application side of the contact arrangement, having at least one planar electrode arrangement, which is embedded in a planar dielectric material, can be supplied with high-voltage signals, and is shielded on all sides against an unobstructed current flow.

Such a planar contact arrangement is known from EP 2 723 447 B1. The dielectric material comprises a central region, from which a spiral strip forming multiple turns forms the edge region of the contact arrangement. To adapt the effective contact area of the contact arrangement on the application side of the dielectric material to an underlying surface with respect to the size, the spirally formed strip can be shortened at a suitable point with the aid of a tool to thus reduce the size of the application surface in the desired manner. In this manner, a dielectric barrier plasma field can be generated in the required size by means of the contact arrangement and can act, for example, on a skin surface of a human or animal body. The skin or another surface to be treated can function in this case as a counter electrode if the body comprising the surface is sufficiently conductive. The electrode is supplied with a high voltage which is sufficient to generate the plasma in an air space between the contact arrangement and the surface to be treated, in particular the skin. In order that a defined air space is produced when the electrode presses against the surface to be treated, the dielectric material can be provided on its application surface with a structure in the form of nubs or a grid or the like, the upper side of which is formed to be applied to the surface to be treated and forms sufficient air intermediate spaces between the application points, surfaces, or lines, in which the dielectric barrier plasma discharge can take place.

After the strip is cut to length, for example, using scissors, the cut edge is wrapped with an insulating contact element, which effectuates a contact with the electrical conductor forming the electrode, for example, by means of cutting contacts. The externally generated high-voltage signal is transmitted to the electrode via the contact element. The formation of the contact arrangement having the spiral strip forming more than one entire turn does permit an adaptation of the effective application area to a special usage case, but results in a certain instability of the application arrangement. In addition, the adaptability of the application area reaches limits if, for example, the treatment is intended for a wound which is not formed substantially circular, but oblong.

The present invention is therefore based on the object of improving a planar contact arrangement of the known type with respect to its stability and adaptability to nonround treatment areas.

To achieve this object, a planar contact arrangement of the type mentioned at the outset is characterized in that the contact arrangement extends with a width in a longitudinal direction and comprises in the longitudinal direction multiple identically constructed sections each having a dielectric material section in the width of the contact arrangement and each having at least one electrode section, wherein the electrode sections of the sections adjoin one another in the longitudinal direction and form an electrode arrangement extending over the entire length, in that at least one section is separable on an intended separation line extending transversely to the longitudinal direction from an adjacent section to reduce the size of the application area in the longitudinal direction, and in that the intended separation line is covered by an insulating component on the remaining adjacent section.

According to the invention, a construction of the planar contact arrangement which is novel in principle is proposed, in which identically constructed sections have a width of the dielectric material which corresponds to the width of the contact arrangement—neglecting possible adhesive attachments. The length of the contact arrangement can be adapted to the respective usage case by the possible separation of one section or multiple sections. The width remains unchanged in this case. Due to the separation of a section along the intended separation line, the associated electrode section protrudes into the separation surface at the intended separation line in the remaining section, which is now an edge section, and could be directly contacted, for example, by a person carrying out the plasma treatment. This is avoided in that the contact arrangement according to the invention covers the intended separation line in the remaining section using an insulating component, which therefore also extends over the width of the dielectric material, thus over the width of the application area of the contact arrangement.

The contact arrangement according to the invention is significant in particular for the treatment of wounds, in particular operation wounds. The contact arrangement can be laid as a wound cover on the skin and adhesively fastened using correspondingly shaped adhesive tabs. At reasonable time intervals, the plasma treatment can then be performed to kill off bacteria in the wound region and/or enhance the micro-circulation in the tissue, without the wound dressing having to be removed. The length of the contact arrangement can be adapted to the length, for example, of an operation incision by the design according to the invention having multiple removable sections.

The width of the sections does not always have to be the same, although generally a constant width of the sections is expedient, in particular for manufacturing reasons. For certain areas of application, however, it can also be reasonable if the width of the sections decreases toward one end or toward both ends.

The longitudinal direction of the contact arrangement is generally a straight line. However, the contact arrangement forming a slight curve with the sections is not precluded, wherein the ends of the contact arrangement are at an angle of a 90°, preferably <60° in relation to one another. The deviation from the straight line which runs through one end is thus to be less than 90°, preferably less than 60° at the other end.

The intended separation lines between the sections, which are aligned transversely to the longitudinal direction, are preferably perpendicular to the longitudinal direction. However, this is not required, because the respective end of the section formed by the intended separation line extending obliquely as a straight line is not precluded. It is furthermore possible that the intended separation line is formed from multiple linear sections which are at an angle to one another, so that the delimitation of the section can be formed in the shape of an arrow, for example. It is also possible to form the intended separation line in a slight curve to enable a rounded end of the contact arrangement.

In an embodiment which is preferred for manufacturing, the identically constructed sections each have equal length in the longitudinal direction. The sections can therefore also have an identical shape and/or dimensioning in addition to the identical construction.

The electrode arrangement embedded in the dielectric material can be formed in a way known per se by at least two electrode areas insulated from one another. The electrode areas extend as strip-shaped areas through the length of the contact arrangement. It is possible in this case that the same high-voltage potential is applied to the electrode areas insulated from one another, so that the surface to be treated, on which the contact arrangement rests, functions as a counter electrode for the plasma formation. This also applies if anti-polar high-voltage signals are applied to the two electrode areas, in particular in the form of rapidly decaying AC voltage pulses, and the surface to be treated represents an average potential (ground potential).

Alternatively, however, it is also possible to use the two electrodes as electrode and counter electrode, so that a plasma field is only formed superficially between the electrode areas.

In one embodiment, the insulating component which covers the intended separation line comprises a connection arrangement for at least two electrode areas insulated from one another. By way of this connection, it is possible to check whether the insulating component is properly applied to avoid a direct accessibility of the electrodes at the intended separation line. The connection of the two electrode areas can be easily checked, for example, by a resistance measurement arrangement. It is thus possible that a controller only enables the supply of high-voltage signals and/or pulses to the electrode arrangement if the insulating component reliably covers the electrode areas opening into the end area of the intended separation line.

In one embodiment of the invention, the contact arrangement is formed over its entire length by the sections and thus exclusively consists of the identically constructed sections. The supply of the high-voltage signals to the electrode arrangement can advantageously take place in this case through the insulating component, which contains a supply arrangement for supplying the high-voltage signals to the electrode arrangement.

The supply arrangement can be a mere contact of the electrode arrangement in this case if the high-voltage signals are generated by an external device and conducted to the supply arrangement.

In another embodiment, the supply arrangement contains a control circuit for generating the high-voltage signals. In this case, it can be sufficient to supply the supply arrangement with solely a normal supply voltage which does not have to be a high voltage.

Furthermore, it is possible that the supply arrangement also contains batteries, from the voltage of which the control circuit generates the high-voltage signals, in addition to the control circuit for generating the high-voltage signals. In this embodiment, the contact arrangement is autonomous and no longer requires an external terminal. The supply arrangement having the batteries is then implemented either in the end section or in the insulating component.

In a further embodiment, sensors for emitting at least one sensor signal for at least one parameter measurable on the application side can be located in the sections of the contact arrangement. The measurement of such parameters can be reasonable in particular in the case of the application to the skin as the surface to be treated. It is thus possible to determine reddened skin, local warm areas, changes of the pH value of the skin, etc. In the case of a wound dressing, local infections can be recognized early by such measurements and a plasma treatment can thus be initiated which counteracts the infection because of the bacteria-reducing effect.

An evaluation arrangement for the sensor signals can be contained in the supply arrangement. Alternatively, however, it is also possible to detect the sensor signals directly at the sensor or to transmit them from the sensor using a transmission cable or wirelessly to a corresponding receiving device. The wireless transmission advantageously takes place in a close-range communication system, for example, according to the Bluetooth standard. An evaluation unit is used for evaluating the sensor signals and giving an alarm if necessary. Furthermore, the treatment using the plasma can be controlled by evaluation of the sensor signals.

The separation of individual sections of the contact arrangement can be assisted in that the dielectric material comprises weakened material areas which facilitate the separation on the intended separation line. The weakened material areas can be notches and other depressions, or also passage holes. Passage holes can only be provided in the regions of the dielectric material in which an electrode area is not located, however, so as not to take the risk of a direct current flow from the electrode supplied with high voltage.

In principle, forming both the dielectric material and also the electrode arrangement as flexible to adapt the application side to irregularities of the surface to be treated, on which the contact arrangement is placed, is known. The flexible formation of the contact arrangement is expedient in particular for the treatment of the skin, including wounds located in the skin region.

The contact arrangement according to the invention can furthermore be provided in a way known per se with numerous passage openings, which are formed continuously in the dielectric material from the contact side to an upper side, wherein the electrode arrangement does not protrude in the region of the passage openings, so that the passage openings form continuous channels having uninterrupted dielectric material walls, so that a direct current flow originating from the electrode arrangement is also precluded in this region. The invention is to be explained in greater detail hereafter on the basis of exemplary embodiments illustrated in the drawing. In the figures:

FIG. 2 shows a second embodiment in the same illustrations as FIG. 1;

FIG. 3 shows a third embodiment in the same illustrations as FIG. 1;

FIG. 4 shows a fourth embodiment having a view from below, a horizontal sectional illustration, and a vertical sectional illustration;

FIG. 5 shows a fifth embodiment in the illustrations as in FIG. 1;

FIG. 6 shows a sixth embodiment in the illustrations as in FIG. 1.

Figure 1:
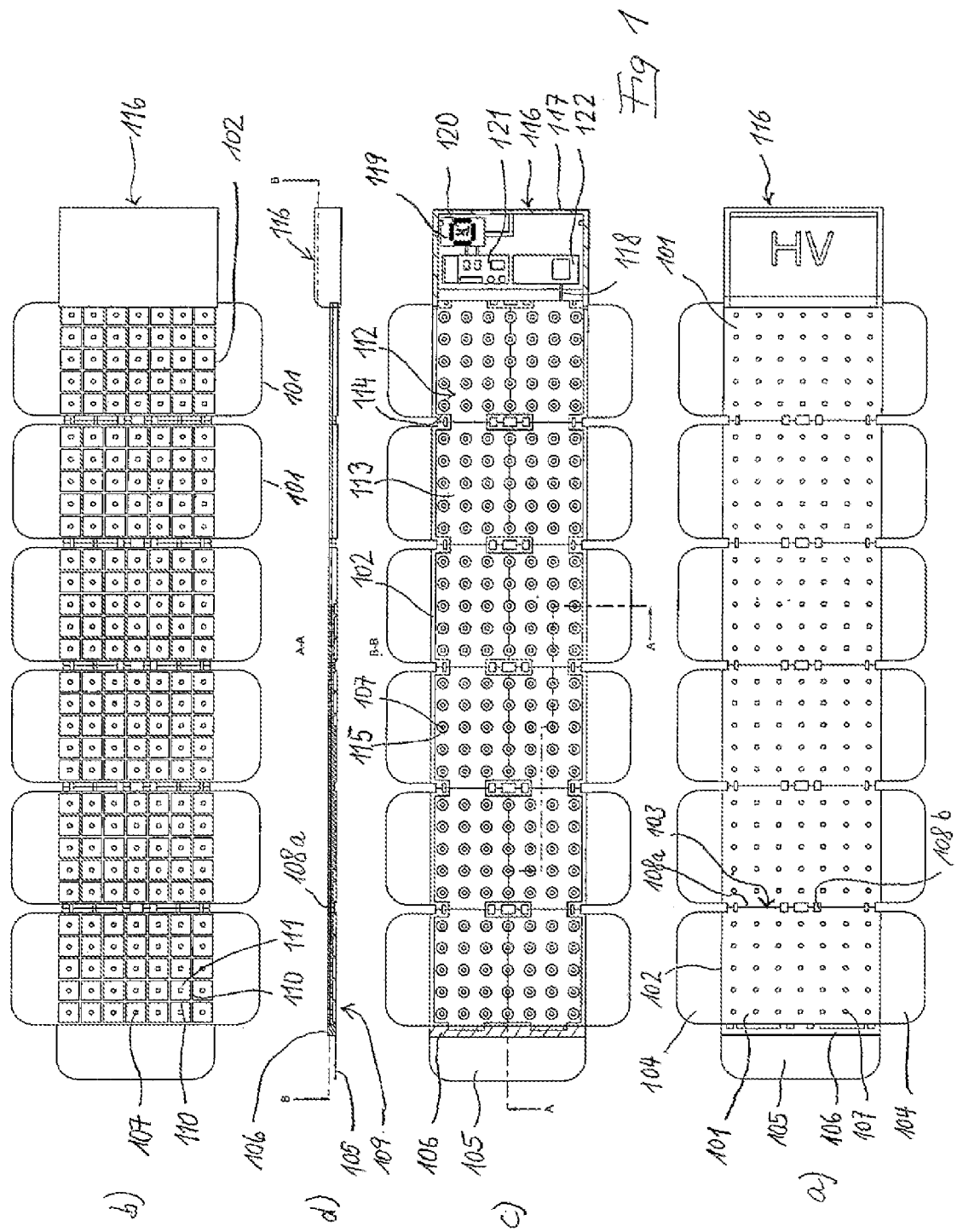
FIG. 1 shows a first embodiment of a contact arrangement having a view from above, a view from below (application side), a horizontal sectional illustration, and a vertical sectional illustration.

It may be seen in the top view of FIG. 1*a*) of the first embodiment illustrated in FIG. 1 that the contact arrangement consists of six essentially identical sections 101, which each comprise a dielectric material 102 on the upper side, which is formed rectangular in the top view in the illustrated exemplary embodiment. The dielectric materials 102 of the sections 101 all have equal width and are attached to one another in a longitudinal direction L via intended separation lines 103. The intended separation lines 103 extend perpendicularly to the longitudinal direction L.

A film-like wing 104 is formed in each case on both sides in the width direction on the dielectric materials 102 of each section 101, which is coated on its lower side using a contact adhesive and is used for fastening the contact arrangement on a surface to be treated, in particular on the skin of a human. The section 101 located at the left end in FIG. 1 additionally comprises a further film-like wing 105, which thus adjoins this section 101 in the longitudinal direction L. To improve the shielding, the wing 105 is attached to the dielectric material 102 of the section 101 via an insulating web 106. The dielectric material 102 of all sections 101 forms a one-piece formation made of the same material with the wings 104, 105 and the insulating web 106. The dielectric material 102 of each section 101 comprises a plurality of regularly arranged passage holes 107, through which wound secretion can be suctioned off if the contact arrangement is used as a wound dressing. In other applications, it is possible to introduce healing or caring agents in liquid or gaseous form into the region of the surface to be treated through the passage holes 107.

The intended separation line 103 comprises weakened material areas 108 in the form of a scored line 108a and in the form of passage openings 108b. With suitable materials for the dielectric material 102, it is possible by way of these weakened material areas to carry out the separation of a section 101 along the intended separation line 103 by tearing off, i.e., without a tool. However, even if scissors are used for the separation, for example, the provided weakened material areas are helpful to carry out the separation along the provided intended separation line 103.

FIG. 1b) shows a view from below, i.e., from an application side 109 of the contact arrangement. On the application side 109, the dielectric material is formed of webs 110, which form a uniform grid and are perpendicular to one another. The webs 110 are formed equal in height, form an application area with the free (lower) edges thereof, and laterally delimit a chamber 111 open to the bottom, i.e., toward the application side 109. The chamber 111 is delimited on top by a continuous layer of the dielectric material 102, in which the passage opening 107 is located centrally in each chamber 111. The chambers 111 can remain empty or can be partially filled, for example, with healing and/or caring substances.

The webs 110 thus form a spacer to form an air volume inside the chambers 111, in which the plasma for the treatment of the surface, in particular for the treatment of the skin, can form.

FIG. 1c) shows a horizontal section along line B-B, as is shown in FIG. 1d). The horizontal section enables a top view of an electrode arrangement 112, which is enclosed on all sides by the material of the dielectric material 102. The electrode arrangement 112 illustrated in FIG. 1 is a planar conductive layer, which forms a single coherent electrode area 113 as a single electrode. The area comprises recesses 114 in the region of the weakened material areas 108 formed as passage openings 108b. Furthermore, it is recognizable that the electrode area 113 also comprises passage openings 115 in the region of the passage openings 107, the diameter of which is larger than the diameter of the passage openings 107 of the dielectric material 102, however. Accordingly, the electrode area 113 does not extend up into the region of the wall of the passage opening 107. The passage opening is thus delimited by a wall which consists in uninterrupted form of the material of the dielectric material 102.

FIG. 1d) shows a vertical section, which also illustrates the formation of the dielectric material 102. The course of the vertical section shown in FIG. 1d) is illustrated by the section line A-A in FIG. 1c).

The contact arrangement formed from the sections 101 is finished in the exemplary embodiment according to FIG. 1 by an insulating component 116, which, as an insulating housing, overlaps the intended separation line 103 of the last section 101 shown on the very right in FIG. 1, so that the electrode area 113 protruding into the end face of the intended separation line 103 of the section 101 is covered by the insulating component 116 in a securely insulating manner. The insulating component 116 contains in this embodiment a supply arrangement 117, via which high-voltage signals are transmitted via a supply line 118 to the electrode arrangement 112. The supply arrangement 117 contains in this case a controller 119 having a microcontroller 120, a signal forming step 121, and a transformer step 122 for forming the high voltage. In this embodiment, a supply voltage is supplied from the outside to the supply arrangement 117, which can be an AC voltage or a DC voltage.

The embodiment illustrated in FIG. 2 substantially corresponds to the embodiment according to FIG. 1, so that only the differences are explained hereafter. The reference signs 1xx used for the embodiment according to FIG. 1 are maintained for the further embodiment as 2xx with the identical part xx. The reference signs are used for the further embodiments in an analogous manner. In the embodiment according to FIG. 2, the electrode arrangement 212 consists of two electrode areas 213a, 213b insulated from one another, which each extend over the length of the contact arrangement. The supply arrangement 217 in the insulating component 216 contains a transformer step 122 having two transformers, which supply the two electrode areas 213a and 213b with high-voltage signals via supply lines 218a and 218b, respectively. The high-voltage signals have an identical form in this case, but are polarized inversely to one another, so that, for example, the electrode area 213a is supplied with a positive high-voltage pulse and simultaneously the electrode area 213b is supplied with a negative high-voltage pulse of the same dimension. In this manner, an amplified differential field results between the electrode areas on the application side 209, although the surface to be treated acts as the ground electrode for both high-voltage pulses. In this manner, the efficiency for the formation of a plasma in the chambers 211 is improved.

Figure 2A:
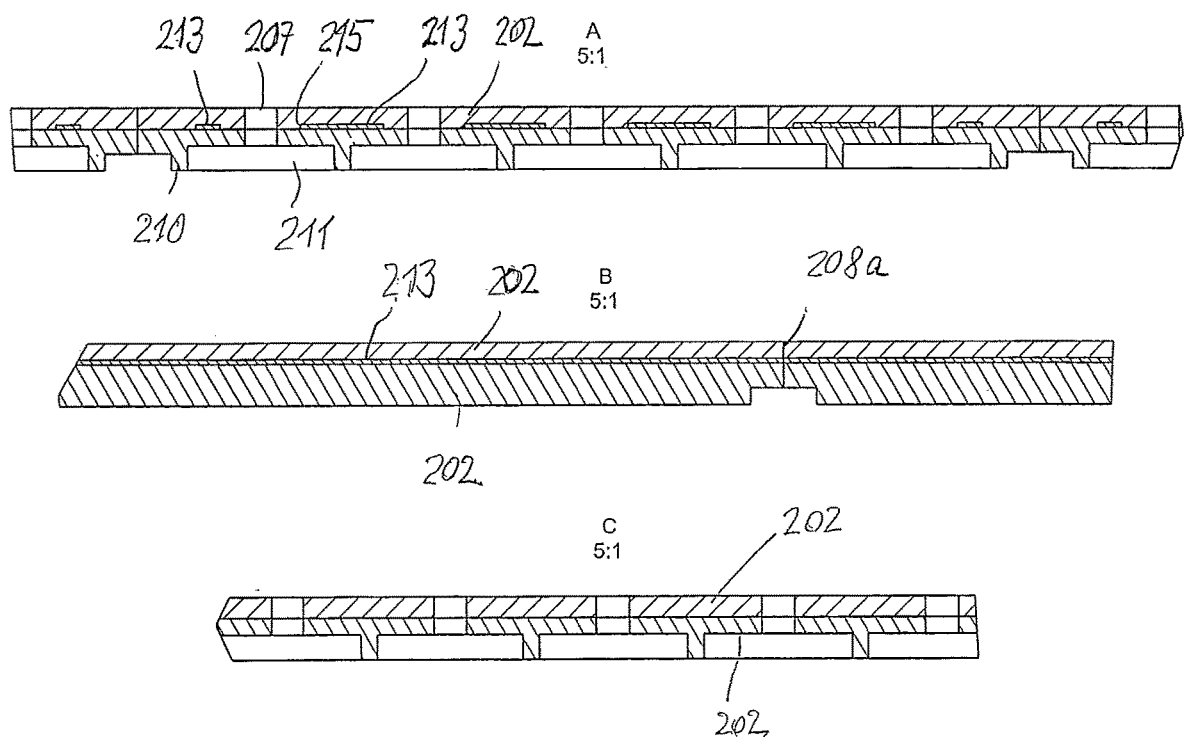
FIG. 2A shows enlarged illustrations of three sections of the vertical section according to FIG. 2*d*)

FIG. 2A contains the vertical section according to FIG. 2d) with markings of detail sections, which are shown as detail A, B, and C in the scale 5:1. The vertical section extends along the section line A-A shown in FIG. 2c).

In the exemplary embodiment illustrated in FIG. 3, which substantially corresponds to the exemplary embodiment according to FIG. 2, four electrode areas 313a, 313b, 313c, 313d are provided, which are insulated from one another and each extend over the length of the contact arrangement. In this case, the electrode areas 313a and 313b are supplied with the high-voltage signals of the one polarization and the electrode areas 313c and 313d are supplied with the high-voltage signals of the inverse polarity via the respective supply lines 318. The surface to be treated is also used as the counter electrode in this arrangement.

In the embodiment illustrated in FIG. 4, the identically appearing illustration of the top view from above has been dispensed with, so that only the illustrations 4b), 4c), and 4d) are provided. The embodiment corresponds to the embodiment according to FIG. 3. In contrast to the embodiment illustrated in FIG. 3, the supply arrangement 417 comprises a controller 419 which also contains three batteries 423 in addition to the microcontroller 420, the signal forming step 421, and the transformer step 422. The other components of the controller 419 can acquire the energy required for the formation of the high-voltage signals autonomously by way of the batteries 423, so that a supply of energy from the outside is not necessary.

The fifth exemplary embodiment illustrated in FIG. 5 functionally corresponds to the fourth exemplary embodiment illustrated in FIG. 4. In contrast to the fourth exemplary embodiment according to FIG. 4, however, the supply arrangement 517 is not located in the insulating component, but rather in an end section 524, which has the same size as the sections 501 in this exemplary embodiment, but is provided with the supply arrangement 517 and the controller 519 having the batteries 523. In this case, the wing 505 arranged in the longitudinal direction is located on the end section 524. The possible separation of sections 501 therefore takes place from the other end. The electrode areas 513a, 513b, 513c, and 513d extending in the end area of the intended separation lines 503 of the last section 501 are covered here by a narrow insulating component 516, which connects at least two of the electrode areas 513a, 513b, 513c, 513d to one another using a connection arrangement (not shown), from which the controller 519 generates a signal which characterizes the proper arrangement of the insulating component 516 at the end of the contact arrangement and can thus be used as the initialization signal for generating the high-voltage signals. The high-voltage signals for the electrode areas 513a, 513b, 513c, 513d are thus only generated when it is ensured that the free intended separation line 503 at the end of the last section 501 is properly covered by the insulating component 516.

It may be seen from FIG. 5d) that the controller 519 in the end section 524 is embedded, preferably potted, in an enlarged material accumulation of the dielectric material 502.

The sixth embodiment illustrated in FIG. 6 corresponds to the embodiment illustrated in FIG. 3, but comprises sensors 625 within a dielectric strip insulating the electrode areas 613b and 613c from one another, using which parameters of the surface to be treated, in particular a skin surface or a wound surface, can be measured and displayed and/or transmitted to the microcontroller 620 in the controller 619. It is thus possible, for example, to measure the oxygen saturation of the blood in the skin layer in a contactless manner and to initiate the plasma treatment if the oxygen saturation falls below a threshold value. Other parameters, such as temperature, reddening because of an infection, pH value, etc. can be established and evaluated and possibly displayed in a similar manner.

The sensors can themselves be used as a display element if they represent a display for a changes or exceeding of a measured parameter because of a physical or chemical reaction. The sensor reaction can be directly optically perceived or also electrically transmitted to an evaluation unit in this case. Alternatively thereto, sensors 625 are usable which require a voltage supply for the function and/or evaluation thereof.

The sensors 625 can be supplied with a supply voltage from the supply arrangement 617, if necessary, and can be designed in such a way that the sensor signals are also wirelessly transmitted via a close-range communication (for example, according to the Bluetooth standard) to an evaluation step.

In all embodiments, the dielectric material 102, 202, . . . is formed by an insulating plastic, in particular castable silicone. The electrode areas 113, 213, . . . are preferably also formed by a castable plastic, which is compatible with the material of the dielectric material 102, 202, . . . i.e., in particular can also be a silicone. The property as a conductive electrode area is implemented in this case by conductive additives to the carrier plastic, which is nonconductive per se. Of course, however, it is also possible to implement the electrode areas by way of a metallic conductive foil.

The invention claimed is:

1. A planar contact arrangement for generating a dielectric barrier plasma, comprising:
    at least one planar electrode embedded in a planar dielectric material, wherein the at least one planar electrode is configured to be supplied with high-voltage signals, wherein the at least one planar electrode is shielded on all sides against an unobstructed current flow, wherein the at least one planar electrode has a width and extends in a longitudinal direction,
        wherein the at least one planar electrode generates a plasma on an application side,
        wherein the at least one planar electrode is adaptable in size, and
        wherein the at least one planar electrode is constructed from multiple identically constructed sections arranged in the longitudinal direction, wherein each of the multiple identically constructed sections has a dielectric section and at least one electrode section,
        wherein each of the at least one electrode section of each of the multiple identically constructed sections adjoin one another in the longitudinal direction and form an electrode arrangement extending over a length,
        wherein at least one section of the multiple identically constructed sections is separable from an adjacent section of the at least one section of the multiple identically constructed sections at a separation line which extends transversely to the longitudinal direction so as to reduce a size of an application area in the longitudinal direction; and
    an insulating component which covers the separation line on a remaining section of the electrode arrangement.

2. The planar contact arrangement as claimed in claim 1, wherein each of the identically constructed sections have an equal length in the longitudinal direction.

3. The planar contact arrangement as claimed in claim 1 wherein the electrode arrangement comprises at least two electrode areas insulated from one another.

4. The planar contact arrangement as claimed in claim 3 wherein said insulating component comprises a connection arrangement which selectively connects the at least two electrode areas insulated from one another.

5. The planar contact arrangement as claimed in claim 1, wherein said length of the planar contact arrangement is formed by the multiple identically constructed sections.

6. The planar contact arrangement as claimed in claim 1 wherein said insulating component contains a supply arrangement for supplying high-voltage signals to the electrode arrangement.

7. The planar contact arrangement as claimed in claim 6 wherein the supply arrangement comprises a control circuit for generating the high-voltage signals.

8. The planar contact arrangement as claimed in claim 7 wherein the supply arrangement contains one or more batteries, and wherein the control circuit generates the high-voltage signals from a voltage from the one or more batteries.

9. The planar contact arrangement as claimed in claim 1, wherein said length of the planar contact arrangement, with the exception of an end section, is formed by the multiple identically constructed sections, and wherein the end section comprises said insulating component and contains a supply arrangement for supplying high-voltage signals to the electrode arrangement.

10. The planar contact arrangement as claimed in claim 9 wherein the supply arrangement comprises a control circuit for generating the high-voltage signals.

11. The planar contact arrangement as claimed in claim 10 wherein the supply arrangement contains one or more batteries, and wherein the control circuit generates the high-voltage signals from a voltage from the one or more batteries.

12. The planar contact arrangement as claimed in claim 1 further comprising one or more sensors for emitting at least one sensor signal for at least one parameter measurable on the application side.

13. The planar contact arrangement as claimed in claim 12 further comprising an evaluation arrangement for the one or more sensor signals contained in a supply arrangement which supplies the high-voltage signals to the electrode arrangement.

14. The planar contact arrangement as claimed in claim 1 wherein the planar dielectric material has one or more weakened material areas which facilitate the separation on the separation line.

15. The planar contact arrangement as claimed in claim 14 wherein the one or more weakened material areas are at least partially passage holes in a region of the planar dielectric material in which an electrode area is not located.

16. The planar contact arrangement as claimed in claim 1 wherein both the planar dielectric material and the electrode arrangement are flexible and are configured for adaptation to irregularities encountered on the application side.

17. The planar contact arrangement as claimed in claim 1 wherein the width of the planar dielectric material is constant over the length of the planar contact arrangement.

* * * * *